(12) United States Patent
Tou

(10) Patent No.: US 6,649,781 B2
(45) Date of Patent: Nov. 18, 2003

(54) RECOVERY OF MINOR COMPONENTS AND REFINING OF VEGETABLE OILS AND FATS

(75) Inventor: Gee Ping Tou, Johor (MY)

(73) Assignee: Palm Specialty Products, SDN. BHD., Johor (MY)

( * ) Notice: Subject to any disclaimer, the term of this patent is extended or adjusted under 35 U.S.C. 154(b) by 0 days.

(21) Appl. No.: 09/871,606

(22) Filed: May 31, 2001

(65) Prior Publication Data

US 2002/0115876 A1 Aug. 22, 2002

(30) Foreign Application Priority Data

Dec. 14, 2000 (MY) ........................................ 20005886

(51) Int. Cl.$^7$ ................................................ C11B 3/00
(52) U.S. Cl. .......................... 554/207; 554/206; 435/67
(58) Field of Search ................................ 554/206, 207; 430/67

Primary Examiner—Deborah D. Carr

(74) Attorney, Agent, or Firm—Wolf, Greenfield & Sacks, P.C.

(57) ABSTRACT

The invention relates to a process for the recovery of minor components and refining of vegetable oils and fats from crude vegetable oils and fats. The said invention describes the following process:

A process for the recovery of minor components and refining of vegetable oils and fats from crude vegetable oils and fats without destroying naturally occurring components, said process comprising the steps of:

a) removal of polar components from the crude vegetable oils and fats using lower alkyl alcohol or any lower alkyl alcohol-water mixture;

b) removal of alcohol from the product obtained in step (a) by distillation;

c) addition of suitable quantity of bleaching earth to the product obtained in step (b) at normal bleaching temperature followed by filtration; and d) deodorization of the product obtained in step (c) at a low temperature.

32 Claims, No Drawings

RECOVERY OF MINOR COMPONENTS AND REFINING OF VEGETABLE OILS AND FATS

RELATED APPLICATIONS

This application claims priority under 35 U.S.C. §119 from Malaysian patent application serial number PI 20005886, filed Dec. 14, 2000.

TECHNICAL FIELD OF THE INVENTION

This invention relates to a process for the recovery of minor components and refining of vegetable oils and fats from crude vegetable oils and fats, in particular, a process for the recovery of minor components and refining of vegetable oils and fats from seed oil, pulp oil and other vegetable matter.

BACKGROUND OF THE INVENTION

Crude palm oil contains less than 5% of free fatty acid (FFA). The main fatty acids are palmitic acid and oleic acid. During fractionation, fatty acid is slightly concentrated in the palm olein. Crude palm oil contains 600–1000 ppm of tocotrienol/tocopherol mixture. The tocotrienol presence in palm oil are γ-tocotrienol, α-tocopherol, α-tocotrienol and δ-tocotrienol in an approximate ratio of 5:2:2:1. Tocotrienol is also enriched in the palm olein during fractionation. Tocotrienol was claimed to be very effective in cholesterol lowering, preventing arteriosclerosis and stroke, inhibits breast cancer cells, protecting the skin against the effects of ultraviolet radiation and as powerful antioxidant.

Typical crude palm oil contains more than 4% of diglyceride. Diglyceride is considered undesirable as it affects crystallization during fractionation. Based on long term human study on feeding of diglycerides-rich cooking oil, diglyceride was said to be able to reduce serum triglycerides, increased serum high density lipoprotein (HDL)-cholesterol and reduction in plasminogen activator inhibitor.

Crude palm oil contains about 500–700 ppm of carotene. The main carotene components are β-carotene and α-carotene. During fractionation, carotene is concentrated in the olein (liquid) fraction. Crude palm olein can contain up to 1500 ppm of carotene whereas crude palm stearin (the solid fraction) has much lower carotene (as low as less than 200 ppm). Consumption of a mixture of natural carotene was claimed to provide protection towards free radical mediated degenerative diseases such as cancer and cardiovascular diseases. It was also claimed that α-carotene but not β-carotene inhibited liver carcinogenesis. It was also claimed that intake of palm carotene inhibits skin peroxidation induced by ultraviolet radiation.

There are patents describing the production of refined red palm oil from crude palm oil. These include U.S. Pat. No. 5,932,261 and Australian Patent Application No. P18770/88. All these patents involved molecular distillation of palm oil at relatively high temperature to remove the fatty acid.

There are also patents describing the production of carotene concentrate from crude palm oil. These include U.S. Pat. Nos. 5,157,132, 6,072,092, 5,019,668 and U.K Patent No. GB2160874A, GB2218989A and GB1515238. Again all these patents involved pretreatment to the free fatty acid, molecular distillation and followed by the process of post treatment such as using adsorbents.

This invention relates to the process of producing refined red oils and fats, carotene concentrate, distilled fatty acid, tocotrienol and sterol concentrate, and diglyceride from carotene-containing natural oils and fats and has particular but not exclusive application to the process of producing these products from crude palm oil and its fractionated products by first removing the polar components prior to transesterification and therefore no post-treatment is necessary after distillation.

This invention has many advantages. It can refine palm oil and palm oil fractionated products without destroying the carotene at a lower vacuum distillation temperature since the polar components including that of odoriferous materials and free fatty acid are removed by alcohol extraction prior to distillation. It also can refine crude palm oil or its fractions into the refined, bleached and deodorized (R.B.D) oils without using degumming agent such as phosphoric acid and deodorized at a significantly lower temperature as most of the free fatty acid and odoriferous materials have been removed.

This invention also enables transesterification to be carried out without pre-esterification of free fatty acid. It also enables production of carotene concentrate without the need of post-distillation treatment such as using adsorbent. As the polar components had been removed from the oil prior to transesterification, the transesterification reaction was carried out without interference from the unsaponifiable matter and carotene remained in the residue. The processes described in the present invention are simpler and cost-effective as compared to that described in other patents on carotene recovery from palm oil. This invention also enables the recovery of FFA, tocotrienol, tocopherol, sterol and diglyceride and other useful minor components of palm oil.

SUMMARY OF THE INVENTION

The object of the present invention is to provide a process for the recovery of minor components and refining of vegetable oils and fats from crude vegetable oils and fats without destroying naturally occurring components in the crude vegetable oils and fats.

Accordingly, there is provided a process for the recovery of minor components and refining of vegetable oils and fats wherein said process is:

A process for the recovery of minor components and refining of vegetable oils and fats without destroying naturally occurring components, said process comprising the steps of:

a) removal of polar components from the crude vegetable oils and fats using lower alkyl alcohol or any lower alkyl alcohol-water mixture;

b) removal of alcohol from the product obtained in step (a) by distillation;

c) addition of suitable quantity of bleaching earth to the product obtained in step (b) at normal bleaching temperature followed by filtration; and d) deodourization of the product obtained in step (c) at a low temperature.

This invention will be clearly understood and apparent with reference to the detailed description which follows.

DETAILED DESCRIPTION OF THE INVENTION

The features and details of the invention, either as steps of the invention or as combinations of parts of the invention will now be described. It will be understood that the particular embodiments of the invention are shown by way of illustration and not as limitations of the invention. The principle features of the invention may be employed in various embodiments without departing from the scope of the invention.

Carotene is non-polar in nature. It is freely soluble in oils and fats. Its solubility in lower alkyl alcohol is low. Natural oils and fats consist mainly of triglyceride, which also has low solubility in lower alkyl alcohol such as methanol and ethanol. Oils and fats are soluble in n-propanol, isopropanol and other lower alkyl alcohol. Addition of water or a mixture of these lower alcohol water mixtures can be used to form two phases in the presence of oils and fats.

By using polar solvent such as lower alkyl alcohol or lower alkyl alcohol-water mixture, the polar components such as FFA, tocopherol, tocotrienol, sterol, triterpene alcohol, mono-glyceride, di-glyceride, glycolipid and phospholipid can be extracted out from oils and fats, remaining the non-polar components such as carotene, squalene and triglyceride.

The oil or fat after lower alkyl alcohol extraction can be subjected to washing with water. Residual solvent and/or water can be vacuum distilled at a temperature less than 100° C. without destroying tocopherol and tocotrienol in the methanol extract. The mixture of FFA, tocopherol, tocotrienol, sterol, triterpene alcohol, mono-glyceride and di-glyceride can be used for their recovery.

A 1-liter crude palm olein of sample was vigorously stirred with methanol at oil to methanol ratios of 1:1, 1:2, 1:3 and 1:4. Table 1 summarizes the results

| Oil: MeOH ratio | Extraction stages | FFA, % | Carotene, ppm | Weight of MeOH extract, g |
|---|---|---|---|---|
| | Initial | 4.30 | 873 | |
| 1:1 | After 1st extraction | 2.56 | 870 | 25.3 |
| 1:1 | After 2nd extraction | 1.67 | 875 | 18.5 |
| 1:1 | After 3rd extraction | 0.98 | 873 | 14.8 |
| 1:1 | After 4th extraction | 0.59 | 904 | 10.0 |
| 1:1 | After 5th extraction | 0.33 | 889 | 7.8 |
| 1:1 | After 6th extraction | 0.21 | 908 | 7.1 |
| 1:1 | After 7th extraction | 0.16 | 906 | 6.9 |
| 1:1 | After 8th extraction | 0.097 | 898 | 5.0 |
| | Initial | 4.20 | 862 | |
| 1:2 | After 1st extraction | 1.82 | 864 | 41.2 |
| 1:2 | After 2nd extraction | 0.73 | 875 | 22.6 |
| 1:2 | After 3rd extraction | 0.32 | 902 | 15.2 |
| 1:2 | After 4th extraction | 0.17 | 895 | 12.0 |
| 1:2 | After 5th extraction | 0.076 | 896 | 8.7 |
| | Initial | 4.26 | 857 | |
| 1:3 | After 1st extraction | 1.49 | 896 | 53.6 |
| 1:3 | After 2nd extraction | 0.44 | 896 | 32.5 |
| 1:3 | After 3rd extraction | 0.17 | 928 | 19.2 |
| 1:3 | After 4th extraction | 0.052 | 937 | 14.2 |
| | Initial | 4.22 | 895 | |
| 1:4 | After 1st extraction | 1.20 | 918 | 34.6 |
| 1:4 | After 2nd extraction | 0.30 | 940 | 21.4 |
| 1:4 | After 3rd extraction | 0.095 | 940 | 9.5 |

The solvent extraction can be carried out at room temperature (about 32° C.). It was observed that carotene content increases after removal of the polar materials. It is understood that other room temperatures can also be used. There is no advantage to carry out the extraction at the methanol refluxing temperature or other temperature between room temperature and methanol refluxing temperature. At methanol refluxing temperature, more neutral oil (triglyceride) was extracted and the carotene content is lower than that of the starting material indicating some deterioration of carotene under those conditions. Table 2 summarizes the methanol extraction that was carried out at the methanol refluxing temperature.

| Oil: MeOH ratio | Extraction stages | FFA, % | Carotene, ppm | Weight of MeOH extract, g |
|---|---|---|---|---|
| | Initial | 4.36 | 897 | |
| 1:1 | After 1st extraction | 2.64 | 864 | 27.0 |
| 1:1 | After 2nd extraction | 1.66 | 874 | 25.5 |
| 1:1 | After 3rd extraction | 0.96 | 861 | 12.6 |
| 1:1 | After 4th extraction | 0.61 | 850 | 10.7 |
| 1:1 | After 5th extraction | 0.34 | 827 | 8.8 |
| 1:1 | After 6th extraction | 0.20 | 823 | 7.5 |
| 1:1 | After 7th extraction | 0.12 | 815 | 7.2 |
| 1:1 | After 8th extraction | 0.083 | 802 | 6.0 |
| | Initial | 4.23 | 885 | |
| 1:2 | After 1st extraction | 1.71 | 898 | 51.4 |
| 1:2 | After 2nd extraction | 0.75 | 871 | 29.6 |
| 1:2 | After 3rd extraction | 0.28 | 894 | 26.6 |
| 1:2 | After 4th extraction | 0.12 | 884 | 18.3 |
| 1:2 | After 5th extraction | 0.042 | 860 | 8.6 |
| | Initial | 4.26 | 892 | |
| 1:3 | After 1st extraction | 1.37 | 905 | 73.0 |
| 1:3 | After 2nd extraction | 0.40 | 896 | 44.1 |
| 1:3 | After 3rd extraction | 0.13 | 886 | 31.6 |
| 1:3 | After 4th extraction | 0.038 | 880 | 17.0 |
| | Initial | 4.18 | 904 | |
| 1:4 | After 1st extraction | 1.02 | 900 | 40.2 |
| 1:4 | After 2nd extraction | 0.24 | 907 | 21.0 |
| 1:4 | After 3rd extraction | 0.071 | 864 | 12.2 |

It is understood that other polar solvents such as other lower alkyl alcohols or their water mixture can also be used as solvent to extract components such as free fatty acid, tocopherol, tocotrienol, sterol, triterpene alcohol, mono-glyceride and di-glyceride) from natural oils and fats.

For lower alkyl alcohol with three or more carbons, such as iso-propanol and n-propanol, addition of water is necessary to form two phases with the oil. Table 3 revealed the effect of water content in isopropanol after the first extraction at room temperature, using the oil to solvent ratio of 1:2. The addition of water at 5% volume to isopropanol is preferred over the higher water content.

| Extraction solvent | FFA, % | Carotene, ppm |
|---|---|---|
| 5% water in iso-propanol | 1.25 | 896 |
| 10% water in iso-propanol | 1.42 | 847 |
| 15% water in iso-propanol | 1.57 | 825 |
| 20% water in iso-propanol | 1.87 | 835 |

The carotene-containing oil after the methanol extraction still contains about 10% methanol. The methanol can be removed by vacuum distillation at a temperature not more than the 65° C. (boiling point of methanol) and the product is refined red palm oil or refined red palm oil fractions such as refined red palm superolein, refined red palm olein and refined red palm stearin. It is understood that anti-oxidants, either natural or synthetic in origin or a combination of both can be added to the red palm oil or its corresponding fractionated products. It is also understood that anti-oxidants, either natural or synthetic in origin or a combination of both can be added to the carotene containing oil before distillation of methanol.

The subsequent carotene-containing oil can be used directly for esterification. In a preferred embodiment, trans-esterification with 6 molar volume of methanol in the presence of 0.5% sodium hydroxide as catalyst is used. It is understood that acid-catalyzed esterification or transesterification with other bases such as sodium methoxide or potassium hydroxide or at other suitable amounts of methanol and/or catalyst can also be used. It is also understood that small amount of vegetable oil such as sunflower oil can be added into the carotene-containing oil prior to distillation or in the residue receiving vessels for collecting the carotene concentrate.

Transesterification process is monitored by high-resolution gas liquid chromatography using Restek Rtx 65TG column with hydrogen as carrier gas. Glycerol-rich layer can be phased separated and drained continuously or when the reaction is toward completion. The reaction is complete when all the triglyceride and diglyceride peaks disappear in the chromatogram.

The methyl ester layer is centrifuged, with or without addition of small quantity of water to remove small quantity of soap and methanol.

The methyl ester layer is then vacuum distilled. In a preferred embodiment, the methyl ester is degassed in a thin film evaporator, and vacuum distilled less than 3 Pa and at less than 160° C. in two stages of short path evaporator. It is understood that degassing can also be carried with short path evaporator or other suitable vacuum distillation unit. It is also understood that distillation of methyl ester can be carried out with different number of evaporator stages. Carotene concentrate is collected as residue.

Methanol in the glycerol layer is distilled at less than 100° C., preferably under vacuum of less than 20,000 Pa. Glycerol is distilled at less than 160° C. under vacuum of 100 Pa. The methanol extract is distilled to remove the methanol. The residual methanol extract is then subjected to degassing and vacuum distillation in short path evaporators. FFA are distilled first, followed by tocotrienols, tocopherol and sterols, and finally diglycerides. In a preferred embodiment, FFA are distilled at about 200° C. under vacuum of 2 Pa, tocotrienol, tocopherol and sterol at less than 220° C. under vacuum of 0.1 Pa, and diglyceride at 271° C. under vacuum of 0.1 Pa.

After methanol removal, the oil after methanol extraction can be processed into R.B.D. oil by treatment with 0.5% of bleaching earth at 90 to 120° C. under partial vacuum, filter and deodorized at 170 to 240° C. under vacuum of 300 to 500 Pa. It is understood that higher dosage of bleaching earth and/or higher deodorization temperature can also be carried out. The oil refined using this process do not need degumming with phosphoric acid, uses less bleaching earth and deodorized at lower temperature as the process had already removed the fatty acid and odoriferous materials prior to refining.

After methanol removal, the oil after methanol extraction can be fractionated or further fractionated. Since most of the diglycerides and unsaponifiable matter have been removed prior to the fractionation process, the crystallization behavior is more predictable as compared to the conventional fractionation of palm oil.

DESCRIPTION OF PREFERRED EMBODIMENTS

The present invention will now be further specifically described by the following examples. All parts and percentages are by weight unless otherwise stated.

EXAMPLE I

Polar materials were extracted from 1 L of crude palm superolein (with 4.20% FFA, 862 ppm of carotene and 5.7% diglyceride) by adding 2 L of methanol and the mixture was stirred vigorously at room temperature for 5 minutes in a suitable container such as 5-L conical flask. The mixture was transferred into a 5-L separating funnel and allowed to settle into two phases. The lower oil phase was collected and placed into a 5-L conical flask. The methanol layer was transferred into a 1-L evaporation flask and rotary evaporated at water bath temperature of 60° C. under vacuum. The yield of methanol extract was 41.2 g, consisting of 59.6% FFA, 1.2% of tocotrienols, tocopherol and sterols and 20.3% diglycerides.

The oil layer (the oil with 1.82% FFA and 864 ppm carotene) which contained about 10% of methanol in it was further added with 2 L of methanol. The second extraction process was repeated as described above. The yield of methanol extract was 22.6 g, consisting of 48.0% FFA, 1.6% tocotrienols, tocopherol and sterols and 24.6% diglycerides.

The oil layer (the oil with 0.73% FFA and 875 ppm carotene) which contained about 10% of methanol in it was further added with 2 L of methanol. The third extraction process was repeated as described above. The yield of methanol extract was 15.2 g, consisting of 26.1% FFA, 2.0% tocotrienols, tocopherol and sterols and 36.4% diglycerides.

The oil layer (the oil with 0.32% FFA and 902 ppm carotene) which contained about 10% of methanol in it was further added with 2 L of methanol. The fourth extraction process was repeated as described above. The yield of methanol extract was 12.0 g, consisting of 12.3% FFA, 1.6% tocotrienols, tocopherol and sterols and 34.6% diglycerides.

The oil layer (the oil with 0.17% FFA and 895 ppm carotene) which contained about 10% of methanol in it was further added with 2 L of methanol. The fifth and final extraction process was repeated as described above. The yield of methanol extract was 8.7 g, consisting of 5.3% FFA, 1.5% tocotrienols, tocopherol and sterols and 35.8% diglycerides.

The oil layer was rotary evaporated. The red palm superolein contained 0.076% FFA and 896 ppm of carotene and 2.8% diglyceride. The red palm superolein can be further subjected to thin film or short path evaporator to further remove traces of fatty acid and volatile matter.

EXAMPLE II

Polar materials were extracted from 1 L of crude palm oil (with 2.71% FFA, 577 ppm of carotene and 4.1% diglyceride) by adding 2 L of methanol and the mixture was stirred vigorously at 40° C. for 5 minutes in a suitable container such as 5-L conical flask. The mixture was transferred into a 5-L separating funnel and allowed to settle into two phases. The lower oil phase was collected and placed into a 5-L conical flask. The methanol layer was transferred into a 1-L evaporation flask and rotary evaporated at water bath temperature of 60° C. under vacuum. The yield of methanol extract was 29.3 g, consisting of 53.3% FFA, 1.2% of tocotrienols, tocopherol and sterols and 21.5% diglycerides.

The oil layer (the oil with 1.09% FFA and 599 ppm carotene) which contained about 10% of methanol in it was further added with 2 L of methanol. The second extraction process was repeated as described above. The yield of methanol extract was 19.2 g, consisting of 37.5% FFA, 1.6% tocotrienols, tocopherol and sterols and 33.8% diglycerides.

The oil layer (the oil with 0.53% FFA and 599 ppm carotene) which contained about 10% of methanol in it was further added with 2 L of methanol. The third extraction process was repeated as described above. The yield of methanol extract was 15.1 g, consisting of 20.9% FFA, 1.4% tocotrienols, tocopherol and sterols and 33.7% diglycerides.

The oil layer (the oil with 0.20% FFA and 604 ppm carotene) which contained about 10% of methanol in it was further added with 2 L of methanol. The fourth extraction process was repeated as described above. The yield of methanol extract was 9.4 g, consisting of 9.3% FFA, 1.3% tocotrienols, tocopherol and sterols and 34.8% diglycerides.

The oil layer (the oil with 0.09% FFA and 609 ppm carotene) which contained about 10% of methanol in it was further added with 2 L of methanol. The fifth and final extraction process was repeated as described above. The yield of methanol extract was 8.5 g, consisting of 5.8% FFA, 1.4% tocotrienols, tocopherol and sterols and 35.9% diglycerides. The oil layer was rotary evaporated. The red palm oil contained 0.043% FFA and 604 ppm of carotene and 1.7% diglyceride. The red palm olein can be further subjected to thin film or short path evaporator to further remove traces of fatty acid and volatile matter.

EXAMPLE III

Polar materials were extracted from 539 g of crude palm superolein (with 4.17% FFA, 804 ppm of carotene and 4.6% diglyceride) by adding 1 L of isopropanol added with 5% (v/v) of water and the mixture was stirred vigorously at room temperature for 5 minutes in a suitable container such as 5-L conical flask. The mixture was transferred into a 5-L separating funnel and allowed to settle into two phases. The lower oil phase was collected and placed into a 5-L conical flask. The isopropanol-water layer was transferred into a 1-L evaporation flask and rotary evaporated at water bath temperature of 70° C. under vacuum. The yield of isopropanol extract was 74.5 g, consisting of 20.8% FFA, 0.7% tocotrienols, tocopherol and sterols and 16.8% diglycerides.

The oil layer (the oil with 2.23% FFA and 894 ppm carotene) which contained about 10% of isopropanol/water in it was further added with 1 L of isopropanol added with 5% (v/v) water. The second extraction process was repeated as described above. The yield of isopropanol extract was 78.1 g, consisting of 9.9% FFA, 0.5% tocotrienols, tocopherol and sterols and 11.3% diglycerides.

The oil layer (the oil with 0.94% FFA and 981 ppm carotene) which contained about 10% of isopropanol in it was further added with 1 L of isopropanol added with 5% (v/v) water. The third extraction process was repeated as described above. The yield of isopropanol extract was 57.6 g, consisting of 4,1% FFA, 0.3% tocotrienols, tocopherol and sterols and 7.2% diglycerides.

The oil layer (the oil with 0.39% FFA and 1064 ppm carotene) which contained about 10% of isopropanol/water in it was further added with 1 L of isopropanol added with 5% (v/v) water. The fourth extraction process was repeated as described above. The yield of isopropanol extract was 43.2 g, consisting of 1.3% FFA, 0.2% tocotrienols, tocopherol and sterols and 4.7% diglycerides.

The oil layer (the oil with 0.12% FFA and 1138 ppm carotene) which contained about 10% of isopropanol/water in it was further added with 1 L of isopropanol with 5% (v/v) water. The fifth and final extraction process was repeated as described above. The yield of isopropanol extract was 41.0 g, consisting of 0.5% FFA, 0.1% tocotrienols, tocopherol and sterols and 3.1% diglycerides.

The oil layer was rotary evaporated. The red palm superolein contained 0.078% FFA, 1250 ppm of carotene and 0.3% diglyceride. The red palm superolein can be further subjected to thin film or short path evaporator to further remove traces of fatty acid and volatile matter.

EXAMPLE IV

Polar materials were extracted from 492 g of crude palm superolein (with 4.66% FFA, 820 ppm of carotene and 4.7% diglyceride) by adding 1L of 95% ethanol and the mixture was stirred vigorously at room temperature for 5 minutes in a suitable container such as 5-L conical flask. The mixture was transferred into a 5-L separating funnel and allowed to settle into two phases. The lower oil phase was collected and placed into a 5-L conical flask. The ethanol layer was transferred into a 1-L evaporation flask and rotary evaporated at water bath temperature of 70° C. under vacuum. The yield of ethanol extract was 22.9 g, consisting of 68.9% FFA, 1.2% of tocotrienols, tocopherol and sterols and 17.7% diglycerides.

The oil layer (the oil with 2.50% FFA and 852 ppm carotene) which contained about 10% ethanol in it was further added with 1 L of 95% ethanol. The second extraction process was repeated as described above. The yield of ethanol extract was 12.4 g, consisting of 46.8% FFA, 1.7% tocotrienols, tocopherol and sterols and 25.6% diglycerides.

The oil layer (the oil with 1.15% FFA and 863 ppm carotene) which contained about 10% of ethanol in it was further added with 1 L of 95% ethanol. The third extraction process was repeated as described above. The yield of ethanol extract was 9.2 g, consisting of 42.3% FFA, 1.7% tocotrienols, tocopherol and sterols and 28.7% diglycerides.

The oil layer (the oil with 0.65% FFA and 867 ppm carotene) which contained about 10% of ethanol in it was further added with 1 L of 95% ethanol. The fourth extraction process was repeated as described above. The yield of ethanol extract was 7.0 g, consisting of 29.3% FFA, 1.8% tocotrienols, tocopherol and sterols and 31.0% diglycerides.

The oil layer (the oil with 0.30% FFA and 888 ppm carotene) which contained about 10% of ethanol in it was further added with 1 L of 95% ethanol. The fifth extraction process was repeated as described above. The yield of ethanol extract was 7.3 g, consisting of 19.0% FFA, 1.7% tocotrienols, tocopherol and sterols and 35.8% diglycerides.

The oil layer (the oil with 0.17% FFA and 862 ppm carotene) which contained about 10% of ethanol in it was further added with 1 L of 95% ethanol. The sixth extraction process was repeated as described above. The yield of ethanol extract was 5.4 g, consisting of 9.9% FFA, 1.4% tocotrienols, tocopherol and sterols and 34.0% diglycerides.

The oil layer (the oil with 0.12% FFA and 871 ppm carotene) which contained about 10% of ethanol in it was further added with 1 L of 95% ethanol. The seventh and final extraction process was repeated as described above. The yield of ethanol extract was 4.7 g, consisting of 3.8% FFA, 1.5% tocotrienols, tocopherol and sterols and 39.3% diglycerides.

The oil layer was rotary evaporated. The red palm superolein contained 0.058% FFA, 854 ppm of carotene and 2.0% diglyceride. The red palm superolein can be further subjected to thin film or short path evaporator to further remove traces of fatty acid or volatile matter.

EXAMPLE V

The oil after final extraction was used for transesterification directly. 3.52 kg of crude palm superolein (carotene content 763 ppm) extracted similar to Example I. After the final extraction, the oil was reacted with 1 L of methanol in the presence of 17.6 g of sodium hydroxide. The reaction took place at the reflux temperature of methanol for 30 minutes. Gas chromatography revealed no trace of triglyceride or diglyceride, indicating that the reaction was completed. The mixture was transferred into a 5-L conical flask and allowed to settle. The lower glycerol layer was drained out. (0.82 kg, containing about 54% methanol). The upper methyl ester layer was washed ten times with one volume of water. The yield of methyl ester was 3.49 kg (99.1% yield). The carotene ester was also 763 ppm.

EXAMPLE VI 24 kg of carotene-containing methyl ester (carotene 763 ppm) was fed into KD6 short path evaporator at the rate of 4.8 kg per hour, degasser at 100 Pa, 120° C., short path evaporator at 0.8 Pa, 130° C., internal condenser at 12° C. Fatty acid methyl ester was collected as residue (95.8% yield) and carotene concentrate was collected as residue (4.3% yield, carotene content 1.56%).

EXAMPLE VII 170.5 g of carotene-containing methyl ester (carotene 1.56%) was fed into KDL5 short path evaporator at the rate of 602 g per hour, short path evaporator at 6 Pa, 155° C., internal condenser at 20° C. Fatty acid methyl ester was collected as residue (81.6% yield) and carotene concentrate was collected as residue (18.4% yield, carotene content 8.6%).

EXAMPLE VIII 4.1 kg of methanol extract (after rotary evaporation of methanol) was degassed using a KDL5 short path evaporator at the rate of 973 g per hour with evaporator at 110° C., 11700 Pa, internal condenser at 15° C. and liquid nitrogen cold trap. The yield of volatile in the cold trap was 0.8%, consisting of methanol and water. 3.7% of distillate, consisting of hydrocarbons and fatty acids were also obtained.

The degassed methanol extract was again fed into KDL5 short path evaporator at the rate of 955 g per hour, short path evaporator at 2 Pa, 195° C., internal condenser at 50° C. FFA was collected as distillate (48.2% yield).

The residue (51.8% yield) was fed again into the KDL5 short path evaporator at the rate of 955 g per hour, short path evaporator at 0.1 Pa, 220° C., internal condenser at 55° C. Tocopherol, tocotrienol, sterol and diglyceride were collected as distillate (10.5% yield). The composition of the distillate were α-tocopherol 1.26%, α-tocotrienol 0.92%, β-tocotrienol 2.27% and δ-tocotrienol 1.46%, campesterol 1.46%, stigmasterol 1.34% and β-sitosterol 4.80%, diglyceride 61.8%.

The residue (89.5% yield) consists of diglyceride 61.72% and the balance were triglyceride, was fed again into the KDL5 short path evaporator at the rate of 633 g per hour, short path evaporator at 0.1 Pa, 271° C., internal condenser at 60° C. Diglyceride was collected as distillate (70.5% yield). The composition of the distillate was mainly diglyceride (84.6%) with the balance as triglyceride.

EXAMPLE IX 1 kg of refined red superolein obtained similar to Example I was divided into 3 equal portions. 0, 0.3 and 0.5% of bleaching earth (Pure-Flo M85/20) were added into the three portions respectively. The samples were bleached at 105° C. for 15 minutes under nitrogen blanket, filtered through Whatman No. 1 filter paper, and steam distilled at 240° C. for 60 minutes at 500 Pa vacuum. The refined palm superolein were determined for Lovibond colour in 133.35 mm (5¼ inch) cell and the readings were 3.6R, 2.8R and 2.6R respectively.

It should be understood that the preceding is merely a detailed description of certain preferred embodiments. It therefore should be apparent to those skilled in the art that various modifications and equivalents can be made without departing from the spirit and scope of the invention. It is intended to encompass all such modifications within the scope of the appended claims.

All references, patents and patent publications that are recited in this application are incorporated in their entirety by reference.

What is claimed is:

1. A process for the recovery of minor components and refining of vegetable oils and fats from crude vegetable oils and fats without destroying naturally occurring components, said process comprising the steps of:
    a) removal of the polar components from the crude vegetable oils and fats using lower alkyl alcohol-water mixture;
    b) removal of alcohol from the product obtained in step (a) by distillation;
    c) addition of bleaching earth to the product obtained in step (b) at normal bleaching temperature followed by filtration;
    d) deodourization of the product obtained in step (c) at a low temperature; and
    e) recovering the minor components and/or the refined vegetable oils and fats.

2. A process for the recovery of minor components and refining of vegetable oils and fats from crude vegetable oils and fats as claimed in claim 1 wherein the addition of bleaching earth is carried out at a temperature of 90–120° C. and the deodourization of the product obtained in step (c) is carried out at a temperature of 170–240° C.

3. A process for the recovery of minor components and refining of vegetable oils and fats from crude vegetable oils and fats as claimed in claim 1 wherein the removal of polar components is achieved by using a methanol acetone mixture.

4. A process for the recovery of minor components and refining of vegetable oils and fats from crude vegetable oils and fats as claimed in claim 1 wherein the vegetable oil and fat is seed oil.

5. A process for the recovery of minor components and refining of vegetable oils and fats from crude vegetable oils and fats as claimed in claim 4 wherein the seed oil is selected from the group consisting of soybean, cotton seed, sunflower seed, peanut, rapeseed, palm kernel, coconut, linseed, sesame, grape seed, safflower seed, cocoa, corn, olive kernel, babassu, Borneo tallow(illipe), mowrah(illipe), walnut, rice bran, shea, fulwah, oat, pumpkin, wheatgerm, hazelnut, almond, evening primrose, mango kernel, sal and kokum.

6. A process for the recovery of minor components and refining of vegetable oils and fats from crude vegetable oils and fats as claimed in claim 1 wherein the vegetable oil and fat is pulp oil.

7. A process for the recovery of minor components and refining of vegetable oils and fats from crude vegetable oils and fats as claimed in claim 6 wherein the pulp oil is selected from the group consisting of palm, olive and avocado.

8. A process for the recovery of minor components from oil extracted from vegetable matter without destroying naturally-occurring components, said process comprising the steps of:
    a) removal of polar components from extracted oil using lower alkyl alcohol or any lower alkyl alcohol-water mixture;

b) removal of alcohol from the product obtained in step (a) by distillation;

c) addition of bleaching earth to the product obtained in step (b) at normal bleaching temperature followed by filtration;

d) deodourization of the product obtained in step (c) at a low temperature; and e) recovering the minor components and/or the refined vegetable oil.

9. A process for the recovery of minor components from oil extracted from vegetable matter as claimed in claim 8 wherein the minor component is carotene.

10. A process for the recovery of minor components from oil extracted from vegetable matter as claimed in claim 8 wherein the vegetable matter is selected from the group consisting of algae, carrot and tomato.

11. A process for the recovery of methyl ester, glycerol and carotene concentrate from crude vegetable oils and fats comprising transesterifying the product obtained from step (a) of claim 1 with a lower alkyl alcohol to give methyl ester, glycerol and carotene; and recovering the methyl ester, glycerol and/or carotene.

12. A process for the production of carotene concentrate as claimed in claim 11 wherein the vegetable oil is selected from the group consisting of palm oil, carrot oil, tomato oil or any other carotene-containing natural vegetable oil and fat.

13. A process for the production of free fatty acid, tocotrienol, sterol and diglyceride from the alcohol extract of crude vegetable oils and fats using the product obtained from step (a) of claim 1, said process comprising the steps of:

(1) short path distillation of alcohol extract after alcohol removal under vacuum to produce free fatty acid;

(2) further short path distillation of the residue obtained from step (1) under vacuum to produce tocotrienol and sterol as distillate and diglyceride as residue;

(3) further short path distillation of the residue obtained from step (2) under vacuum to produce diglyceride concentrate; and (4) recovering the free fatty acid, tocotrienol and sterol and/or diglyceride.

14. A refined vegetable oil and fat obtained using a process as claimed in claim 1.

15. A process for the recovery of minor components from oil extracted from vegetable matter as claimed in claim 9 wherein the vegetable matter is selected from the group consisting of algae, carrot and tomato.

16. A refined vegetable oil and fat obtained using a process as claimed in claim 8.

17. A refined vegetable oil and fat obtained using a process as claimed in claim 10.

18. A refined vegetable oil and fat obtained using a process as claimed in claim 15.

19. A minor component of vegetable oil and fat obtained using a process as claimed in claim 1.

20. A minor component of vegetable oil and fat obtained using a process as claimed in claim 2.

21. A minor component of vegetable oil and fat obtained using a process as claimed in claim 3.

22. A minor component of vegetable oil and fat obtained using a process as claimed in claim 4.

23. A minor component of vegetable oil and fat obtained using a process as claimed in claim 5.

24. A minor component of vegetable oil and fat obtained using a process as claimed in claim 6.

25. A minor component of vegetable oil and fat obtained using a process as claimed in claim 7.

26. A minor component of vegetable oil and fat obtained using a process as claimed in claim 8.

27. A minor component of vegetable oil and fat obtained using a process as claimed in claim 9.

28. A minor component of vegetable oil and fat obtained using a process as claimed in claim 10.

29. A minor component of vegetable oil and fat obtained using a process as claimed in claim 15.

30. A methyl ester, glycerol or carotene concentrate obtained using a process as claimed in claim 11.

31. A carotene concentrate obtained using a process as claimed in claim 12.

32. Free fatty acid, tocotrienol, sterol and diglyceride obtained using a process as claimed in claim 13.

* * * * *

UNITED STATES PATENT AND TRADEMARK OFFICE
CERTIFICATE OF CORRECTION

PATENT NO.    : 6,649,781 B2                                                Page 1 of 1
DATED         : November 18, 2003
INVENTOR(S)   : Gee Ping Tou It is certified that error appears in the above-identified patent and that said Letters Patent is hereby corrected as shown below:

<u>Title page,</u>
Item [73], Assignee, please change from "Palm Specialty Products, SDN. BHD."
to -- SUPERVITAMINS SDN. BHD. Johor Bahru, Malaysia --

Signed and Sealed this

Ninth Day of March, 2004

JON W. DUDAS
*Acting Director of the United States Patent and Trademark Office*